(12) United States Patent
Budidet et al.

(10) Patent No.: US 7,880,015 B2
(45) Date of Patent: Feb. 1, 2011

(54) PROCESS FOR THE PREPARATION OF ANGIOTENSIN II ANTAGONIST

(75) Inventors: Sankar Reddy Budidet, Hyderabad (IN); Senthil Kumar Natarajan, Hyderabad (IN); Venkata Kishore Gowrabathina, Hyderabad (IN); Ramesh Dandala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 107 days.

(21) Appl. No.: 12/309,016

(22) PCT Filed: Jun. 29, 2007

(86) PCT No.: PCT/IB2007/001946

§ 371 (c)(1),
(2), (4) Date: Jan. 2, 2009

(87) PCT Pub. No.: WO2008/004110

PCT Pub. Date: Jan. 10, 2008

(65) Prior Publication Data

US 2009/0281326 A1  Nov. 12, 2009

(30) Foreign Application Priority Data

Jul. 3, 2006  (IN) .................. 1149/CHE/2006

(51) Int. Cl.
*C07D 257/04* (2006.01)
(52) U.S. Cl. ..................................... 548/250
(58) Field of Classification Search ............. 548/250
See application file for complete search history.

(56) References Cited

U.S. PATENT DOCUMENTS

| 5,399,578 | A * | 3/1995 | Buhlmayer et al. ......... 514/381 |
| 7,199,144 | B2 | 4/2007 | Rukhman et al. |
| 7,378,531 | B2 | 5/2008 | Harel et al. |
| 2006/0069268 | A1 | 3/2006 | Denni-Dischert et al. |
| 2006/0258878 | A1 | 11/2006 | Soni et al. |
| 2008/0234490 | A1 | 9/2008 | Sedelmeier et al. |
| 2008/0275096 | A1 | 11/2008 | Harel et al. |
| 2009/0111995 | A1 | 4/2009 | Denni-Dischert et al. |
| 2009/0192318 | A1 | 7/2009 | Radl et al. |

FOREIGN PATENT DOCUMENTS

| WO |    2004/101534 A1 * | 11/2004 |
| WO | WO 2004/101534 A1 * | 11/2004 |
| WO | WO 2005/049587 A1 | 6/2005 |
| WO | WO 2006/058701 A1 | 6/2006 |
| WO | WO 2007/069271 A2 | 6/2007 |

* cited by examiner

*Primary Examiner*—Susannah Chung
(74) *Attorney, Agent, or Firm*—Jay R Akhave

(57) ABSTRACT

The present invention provides a method for the preparation of N-(1-oxopentyl)-N-[[2'-(1H-tetra-zol-5-yl)[1,1'-biphenyl]-4-yl]methyl]-L-valine (Valsartan) which comprises; treating N-[[2'-(1-triphenylmethyl-tetra-zol-5-yl)biphenyl-4-yl]methyl]-L-valine methyl ester (X) with oxalic acid or its hydrates in a solvent to produce N-[[2'-(1-triph-enylmethyl-tetrazol-5-yl)biphenyl-4-yl]methy]-L-valine methyl ester oxalate (Xa) and treating the compound (Xa) with a base in a solvent followed by reacting with valeryl chloride in presence of base in a solvent to produce N-[[2'-(1-triphenylmethyl-tetra-zol-5-yl)[1,1'biphenyl]-4-yl]methyl]-N-valeryl-L-valine methyl ester (XI), de-protecting the compound (XI) using anhydrous acidic conditions to produce N-(1-oxopentyl)-N-[[2'-(1-H-tetrazol-5-yl)[1,1'biphenyl]-4-yl]methyl-L-valine methyl ester (V) followed by treating with base in a solvent to produce Valsartan.

6 Claims, No Drawings

PROCESS FOR THE PREPARATION OF ANGIOTENSIN II ANTAGONIST

FIELD OF THE INVENTION

The present invention relates to an improved process for the preparation of N-(1-oxopentyl)-N-[[2'-(1H-tetrazol-5-yl)[1,1'-biphenyl]-4-yl]methyl]-L-valine of Formula I.

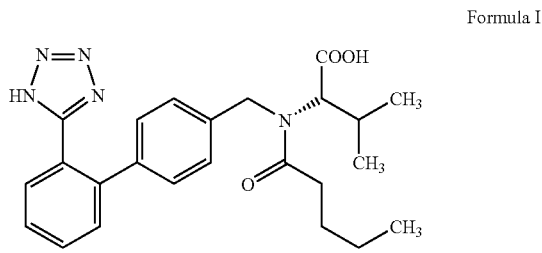

Formula I

BACKGROUND OF THE INVENTION

N-(1-Oxopentyl)-N-[[2'-(1H-tetrazol-5-yl)[1,1'-biphenyl]-4-yl]methyl]-L-valine, generically known as Valsartan, is a nonpeptide, orally active, and specific angiotensin II antagonist acting on the $AT_1$ receptor subtype. Valsartan is used for the treatment of hypertension and is marketed as the free acid under the name DIOVAN®.

Ciba-Geigy has disclosed Valsartan and its pharmaceutically acceptable salts for the first time in U.S. Pat. No. 5,399,578.

U.S. Pat. No. 5,399,578 describes two different processes for the preparation of Valsartan. One of these processes involves the reaction of 4-bromomethyl-2'-cyanobiphenyl (II) with L-valine methyl ester, followed by treatment with valeryl chloride to produce 2-amino-N-[(2'-cyanobiphenyl-4-yl)methyl]-2-methyl-N-valeryl propionate (IV). Compound (IV) is treated with tri-n-butyl tin azide to give N-(1-oxopentyl)-N-[[2'-(1H-tetrazol-5-yl)[1,1'biphenyl]-4-yl]methyl-L-valine methyl ester (V), which is then hydrolyzed under alkaline condition to give finally Valsartan. The process is shown in Scheme-I below:

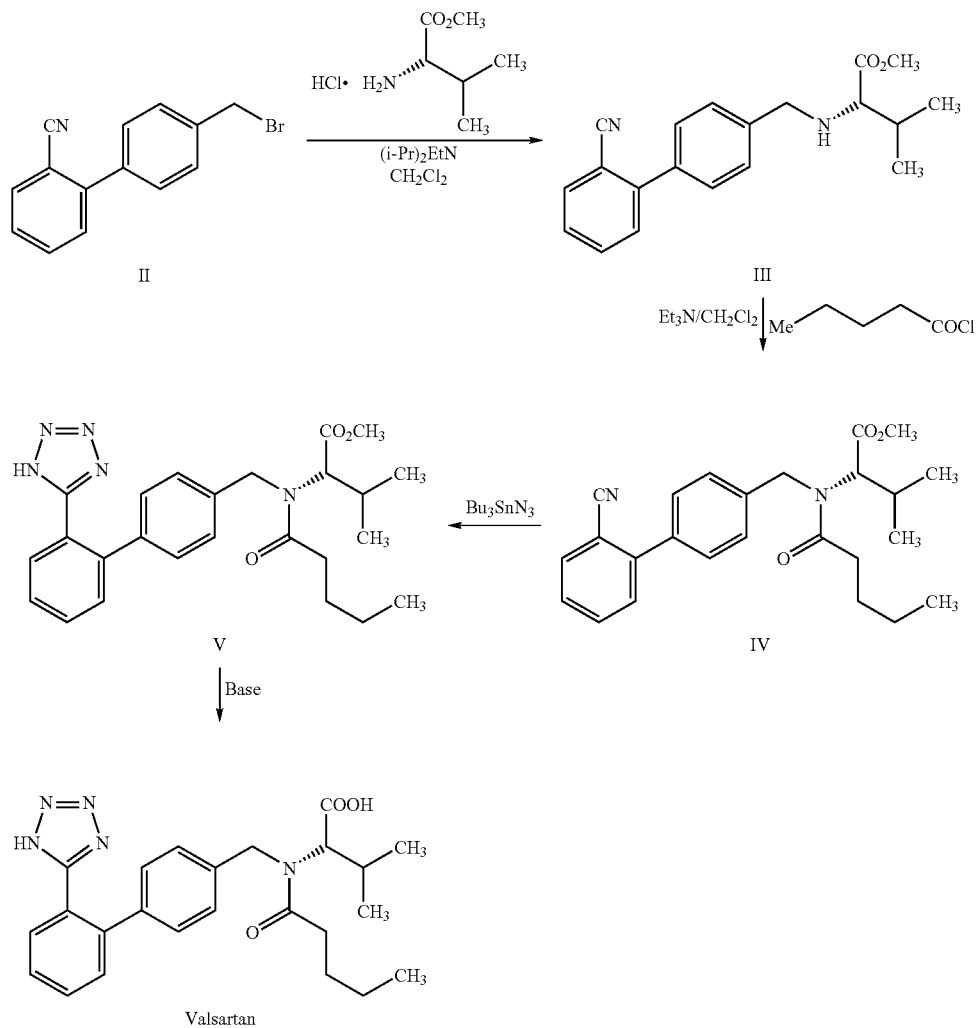

This patent also describes a variant of the above method with using 2-cyano-4-formylbiphenyl instead of 4-bromomethyl-2'-cyanobiphenyl (II).

The disadvantage of the above-mentioned methods is the use of toxic tributyl tin azide to build the tetrazol ring and high demands on safety in order to prevent an explosion due to the formation of hydrogen azide during the reaction.

According to U.S. Pat. No. 5,399,578, Valsartan can also be prepared by reaction of 4-bromomethyl-2'-(1-triphenylmethyltetrazol-5-yl)biphenyl (VI) with L-valine benzyl ester to produce N-[[2'-(1-triphenylmethyltetrazol-5-yl)biphenyl-4-yl]-methyl]-L-valine benzyl ester (VII), followed by treatment with valeryl chloride to produce N-(1-oxopentyl)-N-[[2'-(1-triphenylmethyltetrazol-5-yl)[1,1'-biphenyl]-4-yl]-methyl]-L-valine benzyl ester (VIII). Compound (VIII) is deprotected under acidic conditions to produce N-(1-oxopentyl)-N-[[2'-(1H-tetrazol-5-yl)[1,1'-biphenyl]-4-yl]-methyl]-L-valine benzyl ester (IX), which is then hydrogenated in presence of Pd/C catalyst to give finally Valsartan. The process is shown in scheme II, below:

A major disadvantage of the above method is the fact that all the intermediates except the compound (IX) are oily substances, which can not be crystallized. The final product is therefore, strongly contaminated with undesired compounds and requires repeated crystallization, resulting in a significant loss of yield. Further the use of expensive hydrogenating catalysts like palladium on charcoal for debenzylation is not viable for the commercial point of view.

WO 2004/101534 describes a variation to the above process of preparation of Valsartan, which involves isolation of N-[[2'-(1-triphenylmethyltetrazol-5-yl)biphenyl-4-yl]methyl]valine benzylester (VII) in the form of hydrochloride salt. The hydrochloride salt is further converted to Valsartan.

This process also suffers with major disadvantage of low yield and low purity of N-[[2'-(1-triphenylmethyltetrazoi-5-yl)biphenyl-4-yl]methyl]valine benzylester (VII), which is the key intermediate in the preparation of Valsartan. The reason for such low yield is not described in any of the prior art. We have now found that the reason for the low yield is that the triphenylmethyltetrazol group is highly unstable towards

SCHEME II:

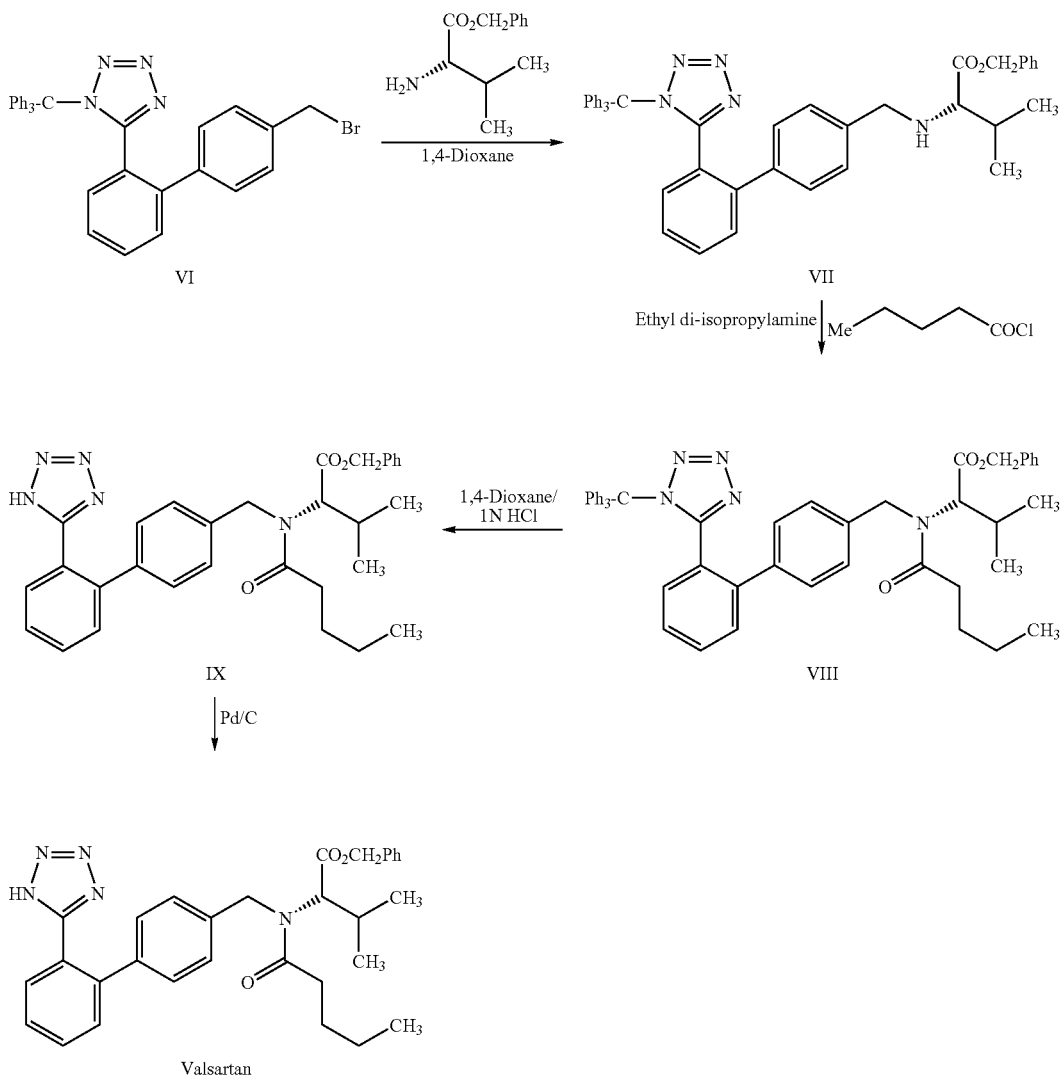

the strong acidic conditions (hydrochloric acid) and undergoes hydrolysis to generate undesired impurities, which get carried forward as impurities in Valsartan (I). Removal of these impurities in the final stage is often proved to be difficult and requires repeated crystallizations, which finally results in the low yield of compound of Formula I.

In the process of the present invention, we have now found that, N-[[2'-(1-triphenylmethyltetrazol-5-yl)biphenyl-4-yl]methyl]valine methyl ester (X) can be purified as its crystalline oxalic acid addition salt (Xa), and can be used as such to produce Valsartan of high purity and yield.

OBJECTIVE OF INVENTION

The main objective of the present invention is to provide a simple and cost-effective process for the preparation of Valsartan of high purity on commercial scale.

SUMMARY OF THE INVENTION

Accordingly, the present invention provides a method for the preparation of N-(1-oxopentyl)-N-[[2'-(1H-tetrazol-5-yl)[1,1'-biphenyl]-4-yl]methyl]-L-valine of Formula I.

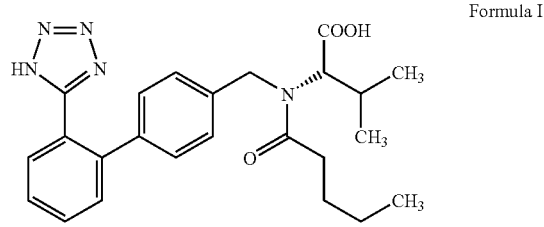

Formula I which comprises;
i) isolating N-[[2'-(1-triphenylmethyltetrazol-5-yl)biphenyl-4-yl]methyl]-L-valine methyl ester (X)

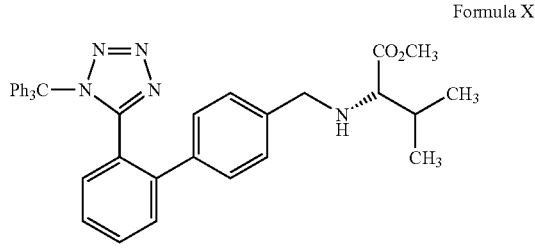

Formula X as an oxalate salt of Formula (Xa),

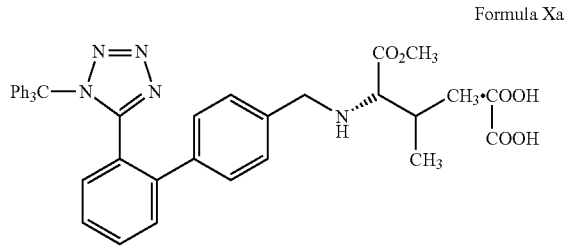

Formula Xa ii) treating the compound of formula (Xa) with a base in a solvent followed by reacting with valeryl chloride in presence of base in a solvent to produce N-[[2'-(1-triphenylmethyltetrazol-5-yl)[1,1'-biphenyl]-4-yl]methyl]-N-valeryl-L-valine methyl ester (XI),

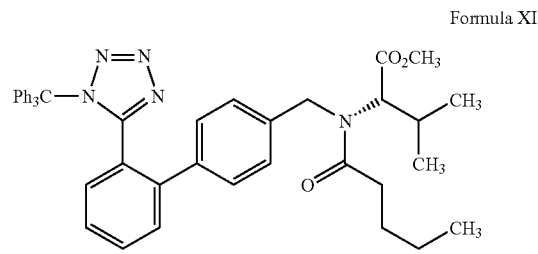

Formula XI iii) deprotecting the compound of formula (XI) using anhydrous acid reagent to produce N-(1-oxopentyl)-N-[[2'-(1H-tetrazol-5-yl)[1,1'-biphenyl]-4-yl]methyl-L-valine methyl ester (V)

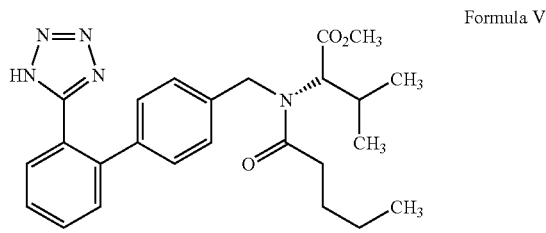

Formula V iv) treating the compound of formula (V) with base in a solvent to produce N-(1-oxopentyl)-N-[[2'-(1H-tetrazol-5-yl) [1,1'-biphenyl]-4-yl]methyl]-L-valine (I).

DETAILED DESCRIPTION OF THE INVENTION

N-[[2'-(1-Triphenylmethyltetrazol-5-yl)biphenyl-4-yl]methyl]valine methyl ester (X) is prepared according to the process described in U.S. Pat. No. 5,399,578. N-[[2'-(1-triphenylmethyltetrazol-5-yl)biphenyl-4-yl]methyl]valine methyl ester (X) is reacted with a molar equivalent of oxalic acid or its hydrates selected from oxalic acid dihydrate in an organic solvent selected from alcohols such as ethanol, n-propanol, isopropanol, n-butanol, isobutanol, methylene chloride, ethyl acetate or mixtures thereof, at a temperature of about −20° C. to about 70° C. and the product obtained is isolated by filtration and dried. The product obtained is purified in a solvent selected from chlorinated hydrocarbons such as methylene chloride, chloroform, 1,2-dichloroethane, preferably methylene chloride to produce N-[[2'-(1-triphenylmethyltetrazol-5-yl)biphenyl-4-yl]methyl]valine methyl ester oxalate (Xa) in crystalline form. It has been observed that preparation of oxalic acid salt of Formula (X) results in greater than 98% purity of product by HPLC analysis.

Treating N-[[2'-(1-triphenylmethyltetrazol-5-yl)biphenyl-4-yl]methyl]valine methyl ester oxalate (Xa) with base selected from organic bases such as triethylamine, diethylamine, diisopropylethyl amine, butylamine or inorganic base such as aqueous solution of alkali metal carbonate such as sodium carbonate, sodium bicarbonate, potassium carbonate, potassium bicarbonate, most preferably aqueous sodium carbonate in a solvent selected from methylene chloride, ethyl acetate, chloroform, carbon tetrachloride, ethylene dichloride, toluene, etc, separating the organic layer containing N-[[2'-(1-triphenylmethyltetrazol-5-yl)biphenyl-4-yl]methyl]valine methyl ester (X), which is further reacted with valeryl chloride in presence of base selected from diisopropylethylamine at a temperature of about 0° C. to about 50° C. and isolated N-[[2'-(1-triphenylmethyltetrazol-5-yl)[1,1'-biphenyl]-4-yl]methyl]-N-valeryl-L-valine methyl ester (XI) after washing. The trityl protecting group of N-[[2'-(1-triphenylmethyltetrazol-5-yl)[1,1'-biphenyl]-4-yl]methyl]-N-valeryl-L-valine methyl ester (XI) is removed by using acid reagent selected from isopropanol hydrogen chloride, methanol hydrogen chloride, ethanol hydrogen chloride to produce N-(1-oxopentyl)-N-[[2'-(1H-tetrazol-5-yl)[1,1'-biphenyl]-4-yl]methyl]-L-valine methyl ester (V), which is further converted to Valsartan using base for hydrolysis.

The following examples illustrate the nature of the invention and are provided for illustrative purposes only and should not be construed to limit the scope of the invention.

EXAMPLE I

Step A: Preparation of N-[[2'-(1-triphenylmethyltetrazol-5-yl)biphenyl-4-yl]methyl]L-valine methyl ester oxalate L-Valinemethyl ester hydrochloride (132.2 g, 0.789 mole) was added to the mixture of 1-triphenylmethyl-5-[4'-(bromomethyl)biphenyl-2-yl]tetrazole (400 g, 0.717 mole) and N,N-dimethylformamide (400 ml) at 20-30° C. Diisopropylethylamine (231.7 g) was added to the reaction mass at 20-30° C. and heated to 45-50° C. The reaction mass was maintained for 16 h at 45-50° C. and concentrated under reduced pressure. The reaction mass was dissolved in ethyl acetate (800 ml) and washed successively with DM water (400 ml) followed by 10% w/w aqueous sodium chloride solution (200 ml) at 20-30° C. The organic layer was diluted with ethyl acetate (1200 ml) and treated with oxalic acid dihydrate (99.5 g, 0.789 mole) at 20-30° C. The reaction mixture was cooled to 0-5° C. and stirred for 1 h at 0-5° C. The solid product was filtered, washed with ethyl acetate and dried to yield N-[[2'-(1-triphenylmethyltetrazol-5-yl)biphenyl-4-yl]methyl]L-valine methyl ester oxalate (420 g).

Step B: Preparation of N-[[2'-(1-triphenylmethyltetrazol-5-yl]biphenyl-4-yl]methyl]-N-valeryl-L-valine methyl ester N-[[2'-(1-Triphenylmethyltetrazol-5-yl)biphenyl-4-yl]methyl]-L-valine methyl ester oxalate (150 g, 0.215 mole) was added to the mixture of toluene (450 ml) and DM water (300 ml), and basified with 10% w/w aqueous sodium bicarbonate solution (450 ml) at 20-30° C. The organic layer was separated and washed successively with DM water (150 ml) followed by saturated aqueous sodium chloride solution. The organic layer was dried over anhydrous sodium sulfate and reacted with valeryl chloride (33.7 g) in the presence of N,N-Diisopropylethylamine (55.6 g) at 0-5° C. The reaction mixture was stirred for 3 h at 5-10° C. and washed with DM water (150 ml), 10% w/w sodium carbonate solution (68 ml) followed by 10% w/w aqueous oxalic acid solution (40 ml). The organic phase was concentrated completely under reduced pressure to dryness to yield N-[[2'-(1-triphenylmethyltetrazol-5-yl]biphenyl-4-yl]methyl]-N-valeryl-L-valine methyl ester as oily mass (141.3 g)

Step C: Preparation of N-(1-oxopentyl)-N-[[2'-(1H-tetrazol-5-yl)[1,1'-biphenyl]-4-yl]methyl]-L-valine methyl ester N-[[2'-(1-Triphenylmethyltetrazol-5-yl)biphenyl-4-yl]methyl]-N-valeryl-L-valine methyl ester (100 g) was added to the mixture of methanol (1 lit) and isopropanol hydrogen chloride (IPA .HCl, 2.75 g; 19% w/w) at 20-30° C. and stirred for 5 h at 0-5° C. The reaction mass was cooled to 0-3° C. and filtered off the solid by-product, trityl methyl ether.

The filtrate was concentrated completely under reduced pressure and the residue dissolved in ethyl acetate (300 ml). The reaction mixture was treated with aqueous sodium carbonate solution (700 ml; 2.5% w/w) at 20-30° C. and separated the aqueous layer. pH of the aqueous layer was adjusted to 8.0-8.3 with 10% w/w aqueous acetic acid and washed with ethyl acetate (100 ml) at 20-30° C. The aqueous layer was separated and acidified with 10% v/v aqueous acetic acid to pH 4.0. The solid product was filtered, washed with water and dried to yield N-(1-oxopentyl)-N-[[2'-(1H-tetrazol-5-yl)[1,1'-biphenyl]-4-yl]methyl]-L-valine methyl ester (47 g).

Step D: Preparation of [N-(1-oxopentyl)-N-[[2'-(1H-tetrazol-5-yl)[1,1'-biphenyl]-4-yl]methyl]-L-valine] (Valsartan)

N-(1-Oxopentyl)-N-[[2'-(1H-tetrazol-5-yl)-[1,1'-biphenyl]-4-yl)methyl]-L-valine methyl ester (19 g) was added to DM water (76 ml) at 20-30° C. and reacted with 22% w/v aqueous sodium hydroxide solution (38 ml) for 5 h at 20-30° C. After completion of reaction, pH of the reaction mass was adjusted to 6.5±0.2 with dilute HCl and washed with ethyl acetate (40 ml). The aqueous phase was treated with activated carbon (1 g) at 20-30° C. and the clear filtrate obtained after removal of carbon was acidified with dilute hydrochloric acid to pH 2.0±0.2 to precipitate the product.

The reaction mixture was cooled to 0-5° C., filtered the product, washed with water and dried under reduced pressure to yield 15.3 g of crude N-(1-oxopentyl)-N-[[2'-(1H-tetrazol-5-yl)[1,1'-biphenyl]-4-yl]methyl]-L-valine (Valsartan) as a white solid. The crude Valsartan was recrystallized from ethyl acetate to obtain pure Valsartan.

EXAMPLE II

Preparation of [N-(1-oxopentyl)-N-[[2'-(1H-tetrazol-5-yl)[1,1'-biphenyl]-4-yl]methyl]-L-valine] (Valsartan)

N-(1-Oxopentyl)-N-[[2'-(1H-tetrazol-5-yl)-[1,1'-biphenyl]-4-yl)methyl]-L-valine methyl ester (45 g) produced as per step (C) of Example I was reacted with 15% w/v aqueous barium hydroxide solution (528 ml) for 10 h at 20-30° C. After completion of reaction, the precipitated solid was filtered, treated with 10% w/v dilute HCl to pH 0.5 to 1.5 in DM water and isolated crude Valsartan.

The crude Valsartan was dissolved in 2.5% w/v aqueous sodium carbonate solution (460 ml) at 20° C.-30° C. and pH was adjusted to 5-7 with 10% w/v hydrochloric acid and then washed with methylene chloride (90 ml). The aqueous layer was acidified with 10% w/v hydrochloric acid and the product was extracted with ethyl acetate (495 ml). The organic layer was separated and ethyl acetate was distilled completely under reduced pressure at 20-60° C. The resulting solid mass was dissolved in ethyl acetate (225 ml) at 40-50° C., cooled to −15 to −20° C., filtered and dried to yield Valsartan (22 g, 99.7% purity by HPLC).

We claim:
1. A process for the preparation of N-(1-oxopentyl)-N-[[2'-(1H-tetrazol-5-yl)[1,1'-bipheny]-4-yl]methyl]-L-valine of Formula I,

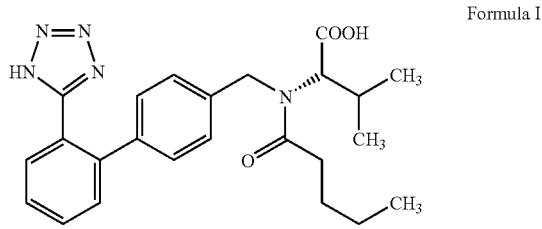

Formula I which comprises:
(i) treating N-[[2'-(1-triphenylmethyltetrazol-5-yl)biphenyl-4-yl]methyl]-L-valine methyl ester Formula (X)

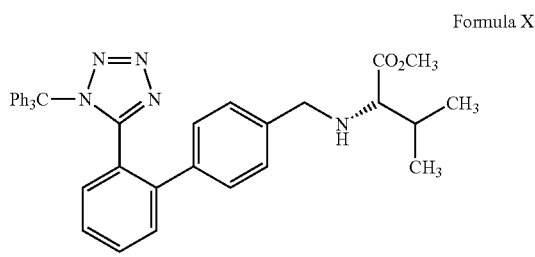

Formula X with oxalic acid or its hydrates in a solvent to produce N-[[2'-(1-triphenylmethyltetrazol-5-yl)biphenyl-4-yl]methyl]-L-valine methyl ester oxalate Formula (Xa),

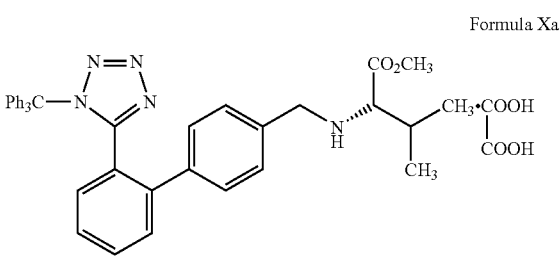

Formula Xa (ii) treating the compound of Formula (Xa) with a base in a solvent followed by reacting with valeryl chloride in presence of base in a solvent to produce N-[[2'-(1-triphenylmethyltetrazol-5-yl)[1,1'-biphenyl]-4-yl]methyl]-N-valeryl-L-valine methyl ester Formula (XI),

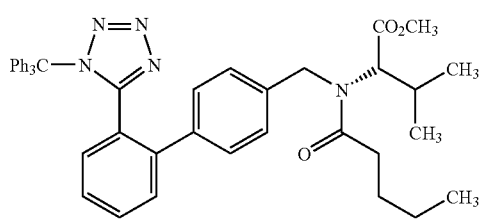

Formula XI (iii) deprotecting the compound of formula (XI) using acid reagent to produce N-(1-oxopentyl)-N-[[2'-(1H-tetrazol-5-yl)[1,1'-biphenyl]-4-yl]methyl]-L-valine methyl ester Formula (V);

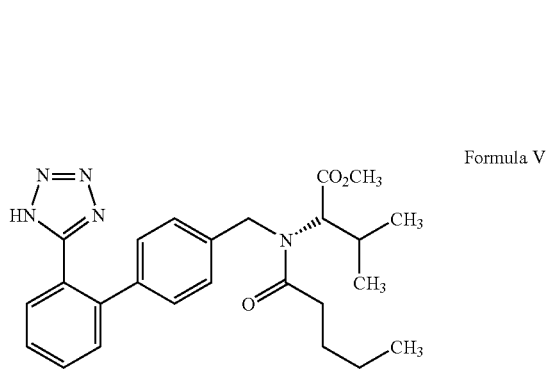

Formula V (iv) treating the compound of formula (V) with base in a solvent to produce N-(1-oxopentyl)-N-[[2'-(1H-tetrazol-5-yl)[1,1'-biphenyl]-4-yl]methyl]-L-valine Formula (I).

2. A process according to claim 1, wherein the solvent used in step (i) is selected from alcohols such as ethanol, n-propanol, isopropanol, n-butanol, isobutanol, methylene chloride, ethyl acetate or mixtures thereof.

3. A process according to claim 1, wherein the base used in step (ii) is selected from organic bases such as triethylamine, diethylamine, diisopropylethyl amine, butylamine or inorganic base such as aqueous solution of alkali metal carbonate such as sodium carbonate, sodium bicarbonate, potassium carbonate, potassium bicarbonate, most preferably aqueous sodium carbonate.

4. A process according to claim 1, wherein the solvent used in step (ii) is selected from methylene chloride, ethyl acetate, chloroform, carbon tetrachloride, ethylene dichloride, toluene.

5. A process according to claim 1, wherein the acid reagent used in step (iii) selected from isopropanol hydrogen chloride, methanol hydrogen chloride, ethanol hydrogen chloride.

6. A process according to claim 1, wherein the base used in step (iv) is selected from aqueous alkali and alkaline earth metal hydroxides such as sodium, potassium, or barium hydroxide.

* * * * *